(12) United States Patent
De Matos Sequeira Berberan E Santos et al.

(10) Patent No.: US 11,525,780 B2
(45) Date of Patent: Dec. 13, 2022

(54) DEVICE AND METHOD FOR MEASURING THE SPATIAL DISTRIBUTION OF THE CONCENTRATION OF COMPOUNDS AND MIXTURES THEREOF IN A FLUID AND/OR THE LEVEL IN A FLUID

(71) Applicant: INSTITUTO SUPERIOR TÉCNICO, Lisbon (PT)

(72) Inventors: Mário Nuno De Matos Sequeira Berberan E Santos, Lisbon (PT); Liliana Marques Martelo, Lisbon (PT)

(73) Assignee: INSTITUTO SUPERIOR TÉCNICO, Lisbon (PT)

( * ) Notice: Subject to any disclaimer, the term of this patent is extended or adjusted under 35 U.S.C. 154(b) by 761 days.

(21) Appl. No.: 16/481,069

(22) PCT Filed: Jan. 24, 2018

(86) PCT No.: PCT/IB2018/050428
§ 371 (c)(1),
(2) Date: Jul. 26, 2019

(87) PCT Pub. No.: WO2018/138649
PCT Pub. Date: Aug. 2, 2018

(65) Prior Publication Data
US 2020/0003687 A1   Jan. 2, 2020

(30) Foreign Application Priority Data

Jan. 26, 2017   (PT) .......................................... 109877

(51) Int. Cl.
*G01N 21/64*      (2006.01)
*G01F 23/292*    (2006.01)
(Continued)

(52) U.S. Cl.
CPC ....... *G01N 21/6408* (2013.01); *B64D 37/005* (2013.01); *G01F 23/292* (2013.01);
(Continued)

(58) Field of Classification Search
CPC .............. G01N 33/22; G01N 33/2829; G01N 33/2835; G01N 33/2841;
(Continued)

(56) References Cited

U.S. PATENT DOCUMENTS 5,043,286 A * 8/1991 Khalil ................ A61K 49/0015
422/82.07
5,198,871 A * 3/1993 Hill, Jr. .............. G01N 21/6402
356/318
(Continued)

*Primary Examiner* — John R Lee
(74) *Attorney, Agent, or Firm* — Mark M. Friedman

(57) ABSTRACT

The invention concerns a method for measuring the concentration of a substance or mixture of substances and/or determining the level in a fluid with intrinsic fluorescence, preferably fuel systems. The invention also refers to the optical device suitable for implementing the method, which comprises a unit which generates light for excitation of the sample; a unit of detection of the signal emitted by the sample and a unit of signal processing.

The device and method by which it is implemented also allow the determination of the spatial distribution of the substance or mixture of liquid substances and/or the fluid level in a container. One of the main applications is the measurement of the concentration of oxygen in the fuel tank of aircrafts, based on the measurement of the intrinsic fluorescence of the fuel.

18 Claims, 4 Drawing Sheets

(51) Int. Cl.
  *G01N 33/28* (2006.01)
  *B64D 37/00* (2006.01)
(52) U.S. Cl.
  CPC ....... *G01N 21/6402* (2013.01); *G01N 21/645* (2013.01); *G01N 33/2841* (2013.01); *G01N 2201/062* (2013.01); *G01N 2201/06113* (2013.01)
(58) Field of Classification Search
  CPC . G01N 2201/0612; G01N 2201/06113; G01N 2201/062; G01N 2021/0684; G01N 21/645; G01N 21/6404; G01N 21/6402; G01N 21/64; G01N 21/6408; G01F 23/292; B64D 37/22; B64D 37/30; B64D 37/04
  See application file for complete search history.

(56) References Cited

U.S. PATENT DOCUMENTS

| | | | | |
|---|---|---|---|---|
| 5,439,797 | A * | 8/1995 | Tsien | G01N 33/582 435/7.1 |
| 7,352,464 | B2 * | 4/2008 | Chen | G01N 21/3504 356/439 |
| 7,385,692 | B1 * | 6/2008 | Nguyen | G01J 3/28 356/301 |
| 7,839,492 | B2 * | 11/2010 | Parks, II | G01N 33/2835 356/70 |
| 8,852,512 | B2 * | 10/2014 | Lam | F02M 21/12 422/68.1 |
| 9,442,070 | B1 * | 9/2016 | Hug | G01N 21/64 |
| 9,709,499 | B1 * | 7/2017 | Crafton | G01N 21/6408 |
| 2004/0090622 | A1 * | 5/2004 | Nielsen | G01N 21/6408 356/317 |
| 2006/0163483 | A1 * | 7/2006 | Chabanis | G01N 21/39 250/339.12 |
| 2006/0262300 | A1 * | 11/2006 | Gylys | G01N 21/8507 356/301 |
| 2007/0114443 | A1 * | 5/2007 | Baltz | G01N 21/645 250/458.1 |
| 2007/0259451 | A1 * | 11/2007 | Heanue | G01N 21/6408 435/287.2 |
| 2009/0141280 | A1 * | 6/2009 | Lam | G01N 21/783 250/361 R |
| 2010/0018119 | A1 * | 1/2010 | Lam | F02M 21/12 250/459.1 |
| 2010/0211329 | A1 * | 8/2010 | Farquharson | G01N 21/3577 702/28 |
| 2010/0255523 | A1 * | 10/2010 | Mik | A61K 49/0021 435/29 |
| 2012/0043477 | A1 * | 2/2012 | Hegazi | G01N 21/274 250/459.1 |
| 2013/0005047 | A1 * | 1/2013 | Mayer | G01N 21/274 73/1.01 |
| 2014/0229010 | A1 * | 8/2014 | Farquharson | G01N 33/22 700/272 |
| 2014/0256593 | A1 * | 9/2014 | Szmacinski | G01N 33/553 435/7.1 |
| 2015/0359472 | A1 * | 12/2015 | Botvinick | A61B 5/1459 600/329 |
| 2016/0245742 | A1 * | 8/2016 | Case | G01N 21/3577 |
| 2016/0334327 | A1 * | 11/2016 | Potyrailo | G02B 6/00 |
| 2018/0171879 | A1 * | 6/2018 | Prociw | B64D 37/00 |
| 2020/0003687 | A1 * | 1/2020 | De Matos Sequeira Berberan E Santos | G01N 21/645 |
| 2020/0148380 | A1 * | 5/2020 | Kwon | G01N 21/85 |

* cited by examiner

DEVICE AND METHOD FOR MEASURING THE SPATIAL DISTRIBUTION OF THE CONCENTRATION OF COMPOUNDS AND MIXTURES THEREOF IN A FLUID AND/OR THE LEVEL IN A FLUID

FIELD OF THE INVENTION

The present invention is within the field of measurement of the concentration of compounds and their mixtures in fluids and/or the level of fluids, in particular the devices and methods for measuring and/or monitoring the spatial distribution of the concentration and the level of a substance or a mixture of several substances. More specifically, the invention relates to devices and methods for measuring and monitoring the concentration of oxygen and/or the level of a fluid with intrinsic fluorescence, preferably in fuel systems.

More particularly, although not exclusively, the present invention can find a specific application in the aerospace industry, for example in fuel systems for jet aircraft, to monitor the concentration of dissolved oxygen in jet fuel or present in the free volume (ullage) of a tank of jet fuel and to measure the level in the fuel tank.

BACKGROUND OF THE INVENTION

Fires and explosions in fuel tanks are one of the main causes of aircraft accidents. In these, the fuel usually contains dissolved air and therefore the fuel typically contains some dissolved oxygen. The air is also present in the free volume between the fuel level and the top of the tank. The amount of dissolved oxygen in the fuel decreases with pressure, and the cruising altitude (low pressure), the oxygen is degassed from the fuel. The fuel-air mixture in the free volume of the tank is susceptible to ignition during the flight, which may be caused by faults in equipment or external attacks. Fuel tank explosions are the result of deflagrations in the free volume when the overpressure of combustion generated exceeds the structural strength of the tank. The protection systems for aircraft fuel tanks are extremely necessary to eliminate or significantly reduce their exposure to flammable vapours.

Fuel tank inerting technology follows the precept of protection that consists of maintaining the oxygen concentration in the free volume below the deflagration limit, thus maintaining the safety of the tank throughout the flight.

For the design of modern aircraft, the American and European standards for the concentration of oxygen in the free volume require less than 9% for military aircraft and less than 12% for commercial aircraft (W. N. Cavage, *Federal Aviation Administration*, 2005, Report No.: DOT/FAA/AIR-05/25). The tank is deemed inert by the European Aviation Safety Agency (EASA) and the *Federal* Aviation Administration (FAA) when the average oxygen concentration within each tank compartment is 12% or less from sea level and up to 10,000 feet altitude, and increasing linearly from 12% to 10,000 feet to 14.5% at 40,000 feet; above that altitude the average oxygen concentration is also extrapolated linearly (European Aviation Safety Agency, *Certification Specifications for Large Aeroplanes CS*-25, Amendment 6, 2009 and Federal Aviation Administration: *Part III Department of Transportation*, Regulation 73 (140), 42444, 2008).

Several technologies for inerting fuel tanks have been developed in recent years, such as: explosion suppression foam, Halon quenching system, liquid nitrogen system, On Board Inert Gas Generation System, OBIGGS), etc. (C. Yan, B. Xueqin, L. Guiping, S. Bing, Z. Yu, L. Zixuan, *Chin. J. Aeronaut.*, 2015, 28, 394-402).

The OBIGGS system is the most widely used on-board technology. On aircraft equipped with OBIGGS, fuel tanks are inerted with nitrogen enriched air (NEA) generated during the flight.

Inert gas (NEA) is produced with compressed air generated by the turbine itself (bleed air), which is passed through an air separation module (ASM), usually consisting of hollow fibre membranes. This module divides the air into a part rich in oxygen, carbon dioxide and water vapour, which is discharged into the atmosphere, and another, rich in nitrogen, which is the NEA inert gas (R. Cherry, K. Warren, *Federal Aviation Administration* 1999; Report No.:DOT/FAA/AR-99/73 and W. M. Cavage, O. Kils, *Federal Aviation Administration* 2002; Report No.: DOT/FAA/AR-02/51). A sensor able to monitor the oxygen concentration in fuel systems or fuel tanks in real time would mean optimizing the functioning of OBBIGS, thereby reducing their wear and fuel consumption.

An established technology to estimate the concentration of oxygen in gases and liquids is electrochemical measurement. The sensor consists of an electrochemical cell having an anode and a cathode immersed in an electrolyte solution. The electrochemical cell is separated by a membrane from the gas or liquid sample whose oxygen concentration is to be measured. The oxygen diffuses from the sample across the membrane into the electrochemical cell to establish equilibrium, and this balance is proportional to the oxygen concentration. A change in the oxygen concentration in the electrolyte causes a change in its electrical properties, with a resulting change in the electric current through the system. The current is proportional to the concentration of oxygen in the electrolyte. The operating limits and the sensitivity of the sensor are defined by the electrolytes used. However, the common electrolytes are not suitable for extreme operating temperatures. In particular, they are not suitable for the low temperatures encountered in aviation applications. In addition, this method requires the use of metal parts inside the tank, which increases the risk of deflagration due to the possibility of sparks.

Another proposed technology in U.S. Pat. No. 5,919,710 (Gord et al.) relates to the measurement of dissolved oxygen in the fuel through the doping of fuel with a luminophore and the subsequent measurement of phosphorescence of this luminophore when excited by a pulse of laser light. The oxygen concentration is related to the lifetime of the radiation emitted by the luminophore. Such a method cannot, however, be seen as a viable and practical method for measuring oxygen concentrations in the fuel in aerospace applications, since the bulk doping in mass of fuels with such luminophores would be impractical.

More recently, oxygen sensors have been developed for aircraft fuel tanks, in which the oxygen concentration is monitored by means of a sensor containing a luminescent substance. Oxygen attenuates the luminescence of the substance and therefore the oxygen concentration can be determined by measuring the light emitted by the luminescent material.

Patent WO 03/046422 describes one such system in which the concentration of oxygen in an aircraft fuel tank is monitored using a material containing a luminescent ruthenium complex.

Patent US 2006/0171845A-1 describes the use of platinum(II) tetrakis(pentafluorophenyl)porphyrin as the phosphorescent compound, which is incorporated in an amorphous fluorinated polymeric matrix and which is used for the detection of oxygen in an aircraft fuel tank. To be appropriate and feasible for use in aircraft fuel tanks the luminescent material must be capable of withstanding the low temperatures reached during the flight, for example –50° C. Moreover, it is desirable that the device is reliable and has a useful life of several years, properties that have not yet been demonstrated by any technology.

Finally, the materials used must be compatible with aviation requirements, in particular that the optical power does not exceed 5 mW/mm² (with an intrinsic safety limit of 35 mW), as specified in the IEC 60079-28:2015 optical standard.

According to the above, there is a need to develop a method for measuring the concentration of oxygen in fuel systems which is capable of withstanding the full range of temperatures during the flight, is reliable, has a service life of several years, has no metal parts inside the fuel tank and can optimize the functioning of the OBBIGS system, thereby reducing wear and fuel consumption.

It has been found, with the method and device that implements the method of the present invention, that it is possible to assess the spatial distribution of the concentration of a substance or a mixture of several substances in a fluid. In particular, the present invention allows monitoring the concentration of oxygen in the aviation fuel tanks using luminescence intensity or the fluorescence lifetime of the fuel itself.

The operating principle of an optical sensor is based on the change of at least one optical property of a given probe (for example: absorption, luminescence, refraction index) in the presence of an analyte. This change is recorded in the device and provides qualitative information about the presence or absence of the analyte, as well as quantitative, allowing enabling the determination the concentration of that analyte. A response based on an optical change offers numerous advantages in sensors. Using very sensitive instrumentation such as luminescence, it is possible to determine very low concentrations of analyte. The response obtained is often rapid, reversible and easy to miniaturize.

An optical sensor can be defined as a device that reacts to an external signal (the analyte) by generating a measurable and reversible optical signal. The reversibility of the signal is an important parameter when it is desired to have continuous measurements, often in real time.

The operation of the optical sensors is based on the effect of the analyte on the processes of absorption, diffusion and light emission. Since electromagnetic radiation has several measurable properties such as wavelength, intensity, polarization and phase, it is possible to measure and relate any change that occurs in these properties with the analyte concentration that we intend to detect. Absorption and luminescence are the phenomena most commonly used in optical sensors. Luminescence measurements are more sensitive than those obtained by variation of absorption, reaching detection limits of approximately $10^{-15}$ mol dm$^{-3}$. The intensity and temporal response of luminescence are the parameters generally used for the detection of a particular analyte, however other parameters can be explored, such as polarization and changes in the shape and position of the spectra.

Conventionally, the measurement of the level of a liquid in a container or tank is done through a buoyant float mechanically or magnetically coupled to an external gauge, an ultrasound or optical transducer that measures the level of liquid, or by using a capacitance sensor that monitors the change in dielectric constant between the plates of a condenser resulting from a change in the liquid level. These methods require, however, the use of metal parts inside the tank or container thereby increasing the risk of deflagration/explosion due to the possibility of sparks, which will depend on the nature of the substance or mixture composed of several substances of interest to be determined.

The use of optical fibre to detect the level in liquids is also well documented. The main advantages of this type of sensor for measuring the levels of a liquid are their passivity, meaning they do not contain moving mechanical parts, and their intrinsic dielectric properties, which means that there is no risk of sparks/deflagrations when used in liquid fuels, and virtually no electromagnetic interference. The most common settings use small prisms mounted at the end of two optical fibres, a conical fibre optic tip that in conical shape or a folded U-shaped optical fibre. In all cases, the probe or fibre optic sensor is suspended or designed to move inside the container. This sensor is potentially fragile and can be damaged by floating debris, vibration or dynamic effects during filling. The potential damage is increased by routine maintenance of the sensor due to biological or chemical scale build-up on the optical surface.

The fibre optic sensors described above are mainly used to measure the level of a liquid in a rudimentary way, that is, to detect whether the tank is empty, full or the level is at some intermediate point. Too large a number of such sensors are required for the continuous measurement of a liquid level, which makes them impractical for the continuous measurement of the level of a liquid in a tank.

Other sensors for measuring the level of a liquid use an optical fibre doped with a fluorescent probe. The main function is to absorb and re-emit light from a source of radiation present in the air. The light is refracted when a fluid of higher refraction index is present in the tank, thus causing the output signal to translate the fluid level. However, this doping of the optical fibre with a fluorescent probe generally, and depending on the liquid to be measured, suffers from leaching and will have to be renewed frequently.

The measurement of distances with active optical methods is well established, when radiation from a source of pulsed or frequency modulated radiation is detected after reflection by the target, which may be the surface of a liquid. The distance is determined from the time elapsed between excitation and detection, in the case of pulsed excitation, or from the resulting lag, in the case of frequency modulated excitation. This method is used to determine the level of liquid in a static tank. However, when the surface of the liquid is a poor reflector, either by absorbing virtually all the incident radiation, or by diffusing it in several directions, as happens with a stirred liquid, the method may be unsuitable and the return signal is erratic and/or too weak.

The measurement of the intrinsic fluorescence of the liquid after optical excitation by the radiation source makes it possible to overcome these problems, with the fluorescence signal from the liquid being measured, also by either of the two methods mentioned.

BRIEF DESCRIPTION OF THE INVENTION

The present invention concerns a method for measuring the concentration of a substance or mixture of substances and/or determining the level in a fluid with intrinsic fluorescence, preferably in fuel systems. The invention further relates to the optical device suitable for implementing the said method, which comprises a sample excitation unit in which excitation light is generated; a unit to detect the signal emitted by the sample and a signal processing unit.

The device and method which it implements further allows the determination of the level and spatial distribution of the substance or mixture of liquid substances in a particular container or tank.

In particular, this invention relates to an optical method and the device that implements the method for measuring and/or monitoring the spatial distribution of the oxygen concentration in fuel systems and/or for determining the level of fuel, since one of the applications is the measurement of the oxygen concentration in the fuel tanks of jet aircraft. In order to mitigate at least some of the problems mentioned above, the present invention provides a method for monitoring the concentration of dissolved oxygen in a fuel or the oxygen concentration in the gas phase present in the free volume above the jet fuel, in a tank.

The method is suitable for the low temperatures found in aviation applications and in fact it applies across the temperature range, from around 50° C. to about −50° C., found in these applications.

As detailed above, the present invention is concerned with the measurement of oxygen concentration and fuel level in fuel systems and enables a solution capable of withstanding the full range of temperatures during the flight; it is reliable, has a service life of several years, does not require metal parts inside the fuel tank, and can optimize the functioning of the OBBIGS system, thereby reducing both wear and fuel consumption.

The present invention has the benefit of using an optical technology in a fuel-rich environment. In contrast, alternative technologies may require the use of electrical power, metal parts and electricity conducting wires. This can introduce an extra risk of ignition in the fuel system. The present method works without any electric current in the regions where there is fuel in liquid or vapour form.

The advantages of this invention relate to the fact that the sensors used are common and low cost. The sensors that constitute the present invention are less hazardous than conventional sensors; they are devoid of electrical components; they are not in direct contact with the mixture where it is intended to evaluate the spatial distribution of compound concentration or other parameters; they are low cost and easily accessible. These sensors are therefore cost-effective and meet regulatory and safety requirements.

DETAILED DESCRIPTION OF THE INVENTION

Figure 1:
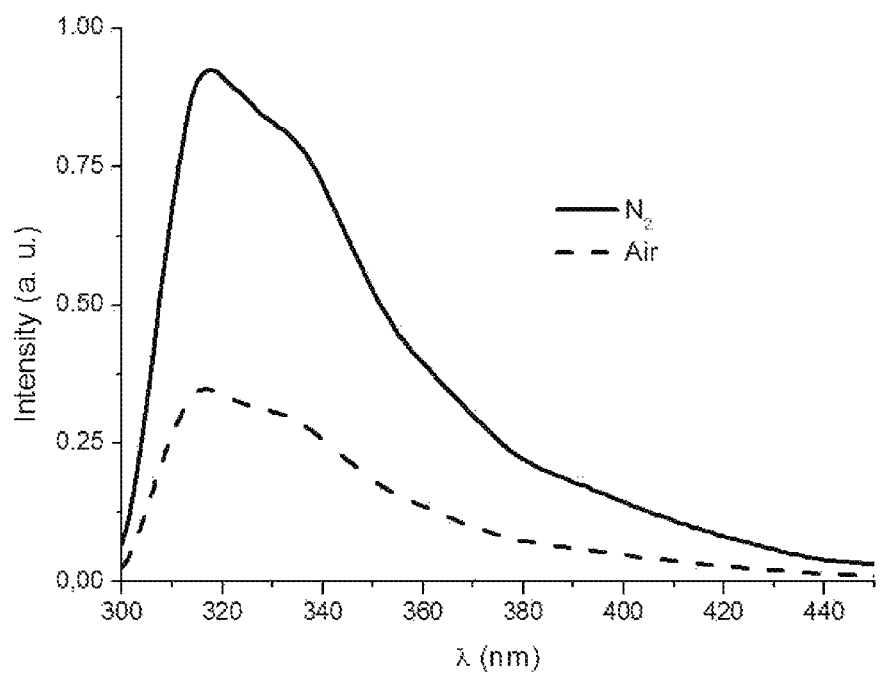
FIG. 1: Jet A-1 fuel emission spectra in the presence (dashed line) and absence (solid line) of oxygen ($N_2$ saturated fuel), obtained at 300 nm excitation wavelength.

The present invention concerns a method for measuring the spatial distribution of the concentration of a substance or mixture of substances in a fluid and/or the level in a fluid, comprising the following steps:
a) irradiation of the fluid with excitation light;
b) detection of light emitted by the fluid and arriving at a detector;
c) emission and digital processing of the signal obtained in the detector, to give the value of the intensity or lifetime of the fluorescence of the fluid;
d) conversion of the lifetime or the fluorescence of fluid into a concentration of a substance or fluid level through a calibration.

In a preferred embodiment, in the method of the invention the fluid is a fluid with intrinsic fluorescence, preferably fuel, and even more preferably, jet aircraft fuel.

In another preferred embodiment, oxygen is the substance whose spatial distribution of concentration is to be measured in the method of the invention.

In another preferred embodiment, the method of the invention is aimed to measure the concentration of oxygen in the fuel systems of jet aircraft, and comprises the following steps:
a) irradiating the liquid fuel or the fuel present in the free volume of the fuel tank with excitation light at a temperature range between approximately −50° C. to about 50° C.;
b) detecting the light emitted by the liquid fuel or the fuel present in the free volume and arriving at a detector;
c) emission and digital processing of the signal obtained at the detector, to give the value of the intensity or lifetime of the fluorescence of the fuel;
d) conversion of the lifetime or the fluorescence of the fuel obtained into a concentration of oxygen through a calibration.

In another preferred embodiment, the method of the invention is aimed to measure the level of jet fuel in a tank, and comprises the following steps:
a) irradiating the liquid fuel of the tank with excitation light;
b) detecting the light emitted by the liquid fuel and arriving at a detector;
c) digital processing of the signal recorded in the detector, obtaining the fluorescence intensity response of the fuel in response to the pulsed or modulated excitation;
d) conversion of the obtained fluorescence signal of the fuel into the liquid level, through calibration and an algorithm.

In another even more preferred embodiment of the invention, the excitation light source can be continuous, modulated or pulsed, more preferably, a light emitting diode (LED) or a laser.

In another even more preferred embodiment of the invention, the excitation light is guided to the fuel via an optical fibre or an optical window, among others.

In another even more preferred embodiment of the invention, the fuel is one of the following: a hydrocarbon-based fuel, a petroleum-derived fuel, Jet A-1, Jet A, Jet B, TS-1, or Jet no. 3, or even better a fuel that comprises kerosene or naphtha/kerosene.

The present invention also concerns an optical device suitable for implementing the method described above and which consists of: a low intensity light source in which an excitation light is generated to irradiate a particular substance or mixture of substances; an optical fibre or optical window to guide the excitation light to the fuel; a photodetector to detect the fluorescence of a substance or mixture of substances; and a signal processing unit.

In a preferred embodiment, the excitation light source can be continuous, modulated or pulsed. In a more preferred embodiment, the excitation light source is a light emitting diode (LED) or a laser.

The present invention also relates to a system for measuring oxygen concentration and/or the fuel level in the fuel tanks of jet aircraft which comprises: the optical device described above and a fuel tank.

The present invention further relates to the use of the optical device described above for the measurement of the spatial distribution of the concentration of a given substance or mixture of various substances and/or the measurement of the level of a fluid.

In a preferred embodiment, the optical device is used to determine the spatial distribution of a substance or a mixture of liquid substances or the level of a fluid in a given reservoir or tank. In an more preferred embodiment, the optical device is used for measuring and/or monitoring of the spatial distribution of the concentration of dissolved oxygen in the liquid fuel or the fuel present in the free volume of a fuel tank, more preferably in jet aircraft.

Unless stated otherwise, "about x" means that any x value presented in the course of the description should be interpreted as an approximate value of actual x value, since such an approximation to the actual value would be reasonably expected by a specialist in technique, due to the experimental and/or measurement conditions that introduce deviations from the actual value.

The term "fuel system" should be taken as the system that stores and distributes the fuel throughout the plane. This system consists of two main parts: fuel tanks and fuel delivery subsystems. The fuel tanks can be independent units or an integral part of the structure. The fuel is taken from the tanks to the engines through fuel lines, control valves and pumps placed along the route, called fuel delivery subsystems.

The term "luminescent substance" should be taken as referring to a substance that is useful in the detection of oxygen in accordance with the invention by means of luminescence and luminescence quenching.

"Luminescence" can be considered as an emission of light which does not result from the temperature of the emitting substance but from the excitation of this substance, for example with incident light.

"Photoluminescence" is the luminescence produced by the absorption of light.

"Luminescence quenching" is the reduction of the luminescence that results from the presence of a quenching substance such as oxygen. Contact with a quenching substance causes the luminescent substance to pass from the excited state to the ground state without emitting light, producing a reduction in the intensity and the respective lifetime of the luminescence.

The term "light", as used herein, includes visible, infrared and ultraviolet radiation. The light emitted by the luminescent substance must be distinguished from the light that is reflected or dispersed by the substance indicated.

Luminescence is usually divided into two forms known as fluorescence and phosphorescence, that are well understood by specialists in the technique. Most of the substances that are luminescent are fluorescent or phosphorescent, but in some cases it is possible that luminescence occurs through a combination of the two mechanisms.

The term "luminophore" refers to an atom or group of atoms in the luminescent substance, responsible for luminescence properties of that substance. The luminescent substance of the invention is the very fuel used in commercial aviation, specifically jet fuel.

"Luminescence decay" is the process by which a substance containing luminophores emits light, after excitation with a short-duration pulse of light (typically tens of picoseconds). In the simplest case, the progressive decrease in the intensity of the light emitted is an exponential function of time, with a characteristic duration determined by the luminescence lifetime ($\tau$).

The term "quenching" is used to refer to a reduction in photoluminescence; in the present invention this is fluorescence. There is a wide variety of quenching processes that diminish the intensity and lifetime of fluorescence of a particular substance. In this case, the quenching is a non-radiative transfer of energy (resonance energy transfer). This process causes the luminescent substance to relax by dissipating the excitation energy through a quencher ("collision") such as molecular oxygen ($O_2$). Oxygen is an effective quencher due to its unusual ground state (triplet state).

Quenching occurs when an oxygen molecule collides (collide means "to be in the vicinity", typically less than 10 nm) with the excited fuel molecule, after which there is a transfer of energy—which thus allows the fluorescent molecule to lose energy without emission. However, since the implementation of the present invention is the issue, the terms are interpreted macroscopically: fluorescence occurs, but the presence of the quencher reduces the number of photons emitted per unit of time, resulting in a reduction of observable fluorescence and its lifetime.

To improve the design and operation of fuel management systems, it is important to measure the concentration of oxygen in the liquid fuel or in the free volume above the fuel in a tank.

In order to mitigate at least some of the problems mentioned above, the present invention provides a method for monitoring the concentration of dissolved oxygen in a fuel or the oxygen concentration in the gas phase present in the free volume above the jet fuel, in a tank.

It has been found that the aviation fuel itself can be used to monitor the concentration of oxygen in the fuel or in the free volume above the fuel, for example in a tank.

The present invention provides an optical method for detecting the dissolved oxygen in jet fuel or in the free volume above the jet fuel, comprising the following steps:

1—irradiating the liquid fuel or the fuel present in the free volume of the tank with excitation light;
2-detecting the light emitted by the liquid fuel or by the fuel present in the free volume and arriving at a detector;
3-digital processing of the signal obtained in the detector, to give the value of the intensity or lifetime of the fluorescence of the fuel;
4-conversion of the lifetime or fluorescence intensity values of the fuel obtained into a concentration of oxygen through a calibration.

The method is suitable for the low temperatures found in aviation applications and in fact it applies across the temperature range, from around 50° C. to about −50° C., found in these applications.

The device that is the subject of the present invention, includes: a low intensity light source, placed so as to irradiate jet fuel, liquid or fuel present in the free volume, and a photodetector, placed so as to detect the fluorescence of the jet fuel. Both the light source and the photodetector are placed outside the fuel tank, the radiation entering and leaving the tank via an optical window or an optical fibre.

The present invention can be advantageously used in inerting applications in aviation as it is a fast and accurate means of monitoring the concentration of dissolved oxygen in the fuel or present in the free volume above it. With the knowledge of the oxygen concentration, an intelligent inerting system can control the injection of nitrogen-enriched air (NEA) to reduce the oxygen concentration and thus reduce the wear of the OBIGGS system and fuel consumption, without the risk of ignition being increased for this reason.

The present invention has the benefit of using an optical technology in a fuel-rich environment. In contrast, alternative technologies may require the use of electrical power, metal parts and electricity conducting wires. This can introduce an extra risk of ignition in the fuel system. The present method works without any electric current in the regions where there is fuel in liquid or vapour form.

The concentration of dissolved oxygen in jet fuel can also be monitored indirectly by using a portion of the fuel located above the liquid fuel (the oxygen concentration in the free volume is related to the concentration of oxygen in the liquid fuel, assuming equilibrium conditions).

The method of this invention is based on the irradiation of jet fuel with light and the measurement of the intensity or lifetime of the fluorescence of the jet fuel, for different oxygen concentrations.

The fuel can be irradiated by one of the following means: optical fibre, optical window, among others.

The intensity of the light emitted by the jet fuel can be measured with an appropriate photodetector, such as a photodiode, CCD (charged couple device), etc., as is well known in the technique.

The excitation source can be continuous, modulated or pulsed, for example, a LED (light-emitting diode) or a laser.

The measurement is associated with a signal processing unit to generate and emit a signal derived from the intensity detected by the photosensor, in response to the irradiation of the jet fuel by the light source.

In one form of implementation, the method of this invention can be used for spot measurements of the oxygen concentration. Alternatively, the method can be used to continuously monitor the concentration of dissolved oxygen in the fuel or the fuel present on the free volume above the fuel.

In one form of implementation, the fuel is a hydrocarbon-based fuel containing polycyclic aromatic hydrocarbons. In another form of implementation of this invention, the fuel can be a petroleum-derived fuel. Still another form of implementation of this invention, the fuel can compromise kerosene. In yet another form of implementation, the fuel can comprise naphtha/kerosene. In the preferred form of implementation of this invention, the fuel is a jet aircraft fuel. This can be Jet A-1 fuel, suitable for most turbine engine aircraft, but also, for example, Jet A, Jet B or TS-1, the main fuel available in Russia and the Commonwealth of Independent States (CIS), as well as Jet fuel no. 3, the main export-grade Chinese fuel, essentially the same as Jet A-1.

Initial analyses consist of jet fuel exposed to air, the oxygen present having the effect of reducing the fluorescence intensity when the jet fuel is irradiated with ultraviolet light (UV) or visible light (250-400 nm). By passing a stream of nitrogen through the jet fuel, the dissolved oxygen in the jet fuel is drastically reduced, the fluorescence emission increases significantly (FIG. 1).

FIG. 1 shows the results obtained for the increase in the emission intensity from the jet fuel with the removal of oxygen. Typically, in the wavelength range of 330-450 nm (covering the spectral range for the Jet A-1 fuel emission), the quenching of the fluorescence emission due to the oxygen present in the air is about 63% at a temperature of 26° C. and a pressure of 1 atm, which corresponds to the maximum concentration that is likely to be encountered in an aircraft fuel tank.

For the calibration of the lifetime of a given substance or mixture consisting of several substances dissolved in a liquid or in the free volume in a tank, the Stern-Volmer equation can be used in the event of suppression of luminescence lifetime:

$$\tau_0/\tau = 1 + k_q \tau_0 [\text{supressor}] \quad (\text{eq. 1})$$

where [suppressor] is the suppressor concentration, $k_q$ is a second order rate constant that is temperature dependent, and $\tau_0$ is the fluorescence lifetime in the absence of oxygen at the temperature in question. The same relationship is valid for the calibration of the intensity, replacing $\tau_0/\tau$ with $I_0/I$, where $I_0$ is the intensity in the absence of a suppressor.

It is possible to use the Stern-Volmer equation for the calibration of the lifetime of the jet fuel for different oxygen concentrations:

$$\tau_0/\tau = 1 + k_q \tau_0 [O_2] \quad (\text{eq. 2})$$

where $[O_2]$ is the concentration of oxygen, $k_q$ is a second order rate constant that is temperature dependent, and $T_0$ is the fluorescence lifetime in the absence of oxygen at the temperature in question. The same relationship is valid for the calibration of the intensity, replacing $\tau_0/\tau$ with $I_0/I$, where $I_0$ is the intensity in the absence of oxygen.

Figure 2:
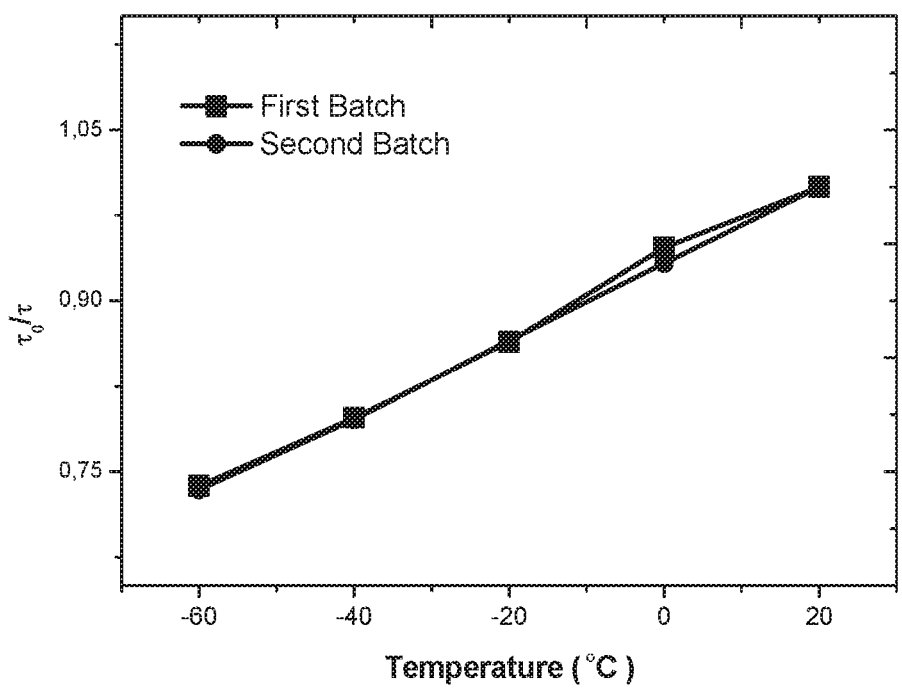
FIG. 2: Relative lifetime graph for deoxygenated samples (two different batches of Jet A-1 fuel) under study at different temperatures. $\tau_{20}$ is the lifetime at 20° C.

The fluorescence lifetime measurements provide specific numerical parameters that are only slightly dependent on the provenance of the jet fuel, as can be seen in FIG. 2.

In fact, as seen in FIG. 2, the response to temperature of the relative fluorescence lifetime of the fuel is the same for two different batches of Jet A-1 fuel, thus showing that the method is not dependent on the jet fuel source.

Figure 3:
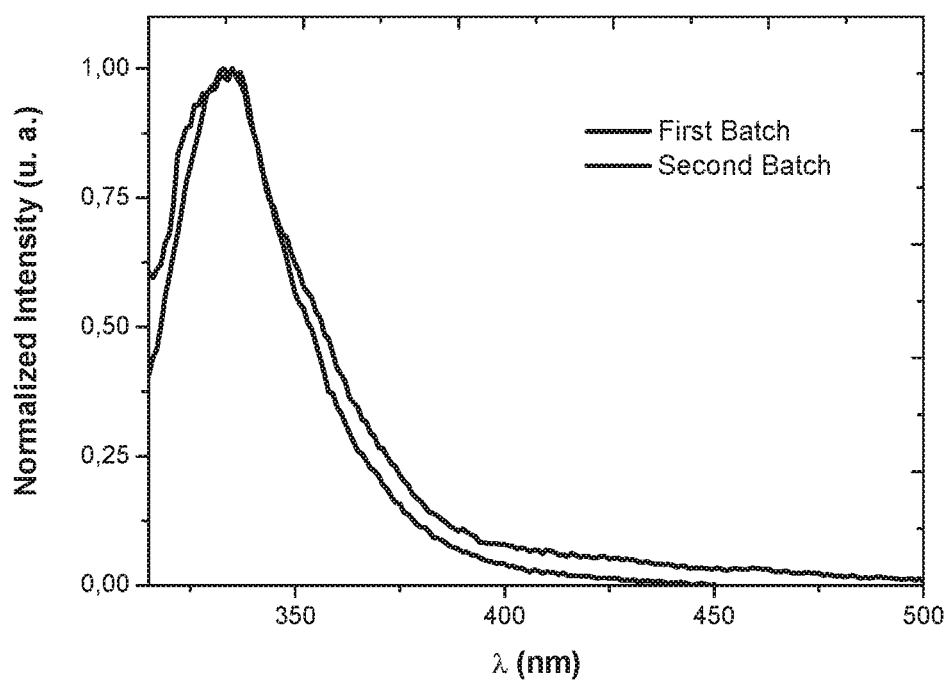
FIG. 3: Identical emission spectra for two different samples (batches) of Jet A-1 fuel (300 nm excitation wavelength).

Identical emission spectra are observed for two different batches of Jet A-1 fuel, proving once again that the method is not influenced by the fuel source, as seen in FIG. 3.

EXAMPLES

Example 1

Figure 4:
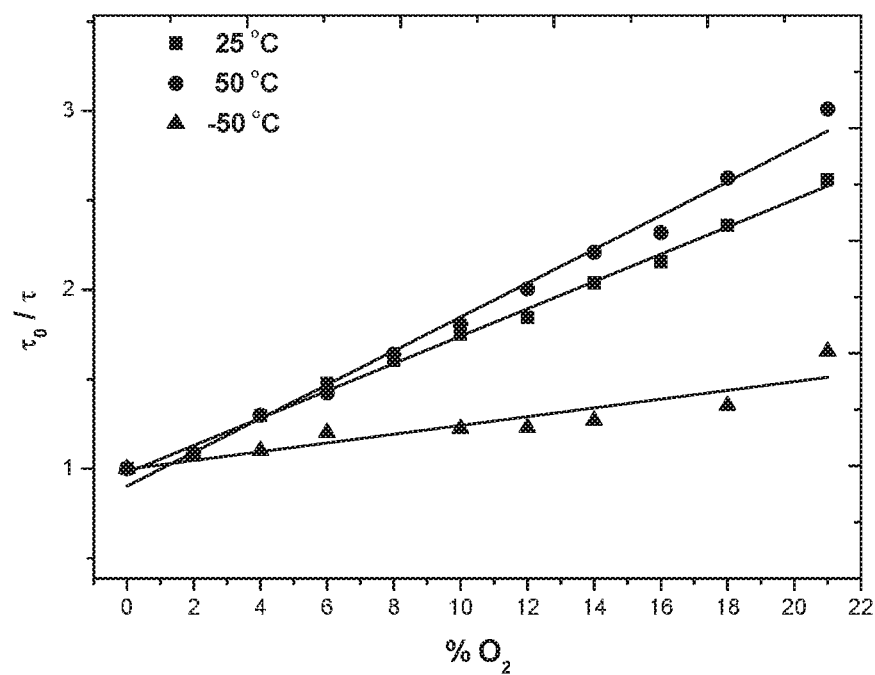
FIG. 4: Stern-Volmer representation of the Jet A-1 fuel lifetimes for different percentages of oxygen at three different temperatures: −50° C., 25° C. and 50° C.

A decrease in temperature produces an increase in the fluorescence lifetime of pure Jet A-1 fuel, FIG. 4. The Stern-Volmer representation of the luminescence lifetimes is practically linear, with a temperature-dependent slope, FIG. 4. The concentration of oxygen at any temperature can be measured and monitored on the basis of this relationship.

This relationship was obtained experimentally as follows: pure Jet A-1 fuel was placed in a 1 cm optical path quartz cell that is sealed with a silicone stopper. The empty space above the fuel contains a controlled composition $N_2/O_2$ mixture (percentage of oxygen between 0% and 21% by volume). The composition of the gaseous mixture was controlled using a gas flow mixer. The fluorescence lifetime of the pure Jet A-1 fuel was measured for the different percentages of oxygen. The Jet A-1 fuel fluorescence lifetime was determined by single-photon counting spectroscopy with a system consisting of a Tsunami Spectra Physics (Ti: Sapphire) picosecond laser (80 MHz repetition rate, 100 fs pulses, 700-1000 nm) and a Coherent 701-2 Rhodamine 6G dye laser from (560-610 nm) or DCM (620-700 nm), with synchronous pumping by a Coherent Innova 440-10 ionized argon laser. The excitation pulses have a duration of 3 to 4 ps with a repetition ratio of 1.9 MHz. The excitation wavelength used was typically 300 nm. Fluorescence emission was measured with a polarizer placed at an angle of 54.7° (magic angle) and recorded at 345 nm. The scattered light is eliminated by a cut-off filter and the light emitted is selected by a Jobin-Yvon HR320 monochromator with a diffraction grating of 100 lines/nm and measured by a Hamamatsu MCP 2809U-01 photomultiplier. The instrumental response function (IRF) has a half-height width of 39 ps.

At a temperature of 25° C. the fluorescence lifetime measured in the absence of oxygen was 39 ns, and for the highest oxygen concentration (21%) it was 15 ns.

Example 2

Figure 5:
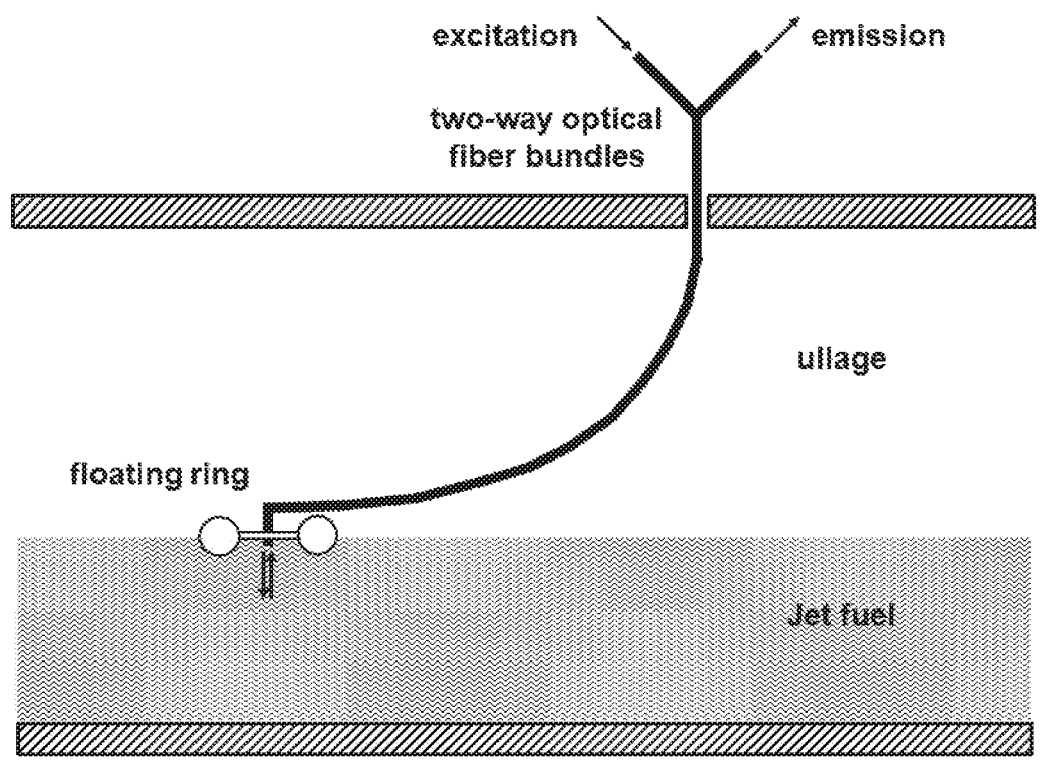
FIG. 5: Schematic representation of the system for measuring oxygen concentration in a fuel tank, using a flexible fibre-optic bundle terminating in a float.

An implementation of the system for measuring dissolved oxygen in jet fuel, close to the surface, and in equilibrium with the oxygen present in the free volume, consists of the assembly in FIG. 5. The excitation light (pulsed, modulated or continuous) enters through an optical fibre and is led to the fuel. The emission from the fuel is collected by another optical fibre and brought to the detector. It is ensured that the emission comes from fuel close to the surface using a bundle of flexible fibres which terminates in a floating ring. The bundle is long enough to reach the bottom of the tank.

Example 3

Figure 6:
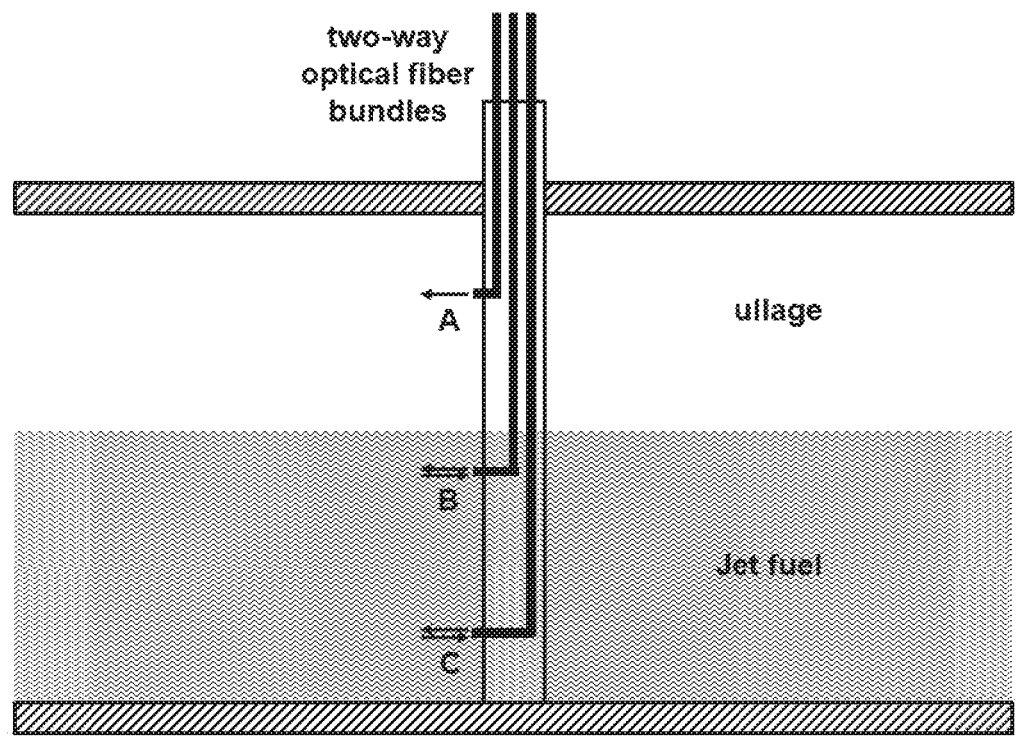
FIG. 6: Schematic representation of the system for measuring oxygen concentration in a fuel tank, using a fixed column containing fibre-optic bundles terminating at various levels. The points A, B and C are points at different heights in the tank.

Another implementation of the system for measuring dissolved oxygen in jet fuel and in equilibrium with the oxygen present in the free volume, consists of the assembly in FIG. 6. The excitation light (pulsed, modulated or continuous) enters through bundles of optical fibres and is led to the fuel, at various tank heights (points A, B and C), through a fixed non-metal column, which supports the bundles of fibres. The emission from the fuel is collected at various heights (points B and C in the example) and brought to the detector.

Example 4

Figure 7:
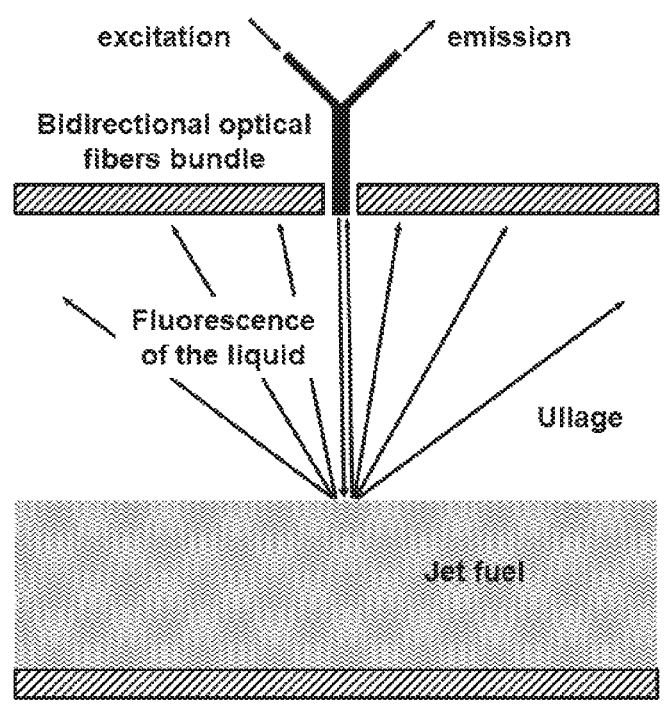
FIG. 7: Schematic representation of the system for measuring the level in a fuel tank, using a radiation source and a detector connected to the top of the tank by optical fibres.

An implementation of the system for measuring the level of fuel in a tank consists of the assembly in FIG. 7. The excitation light (pulsed or modulated) enters through an optical fibre and crosses the tank in a linear path, until it strikes the surface of the fuel. The emission from the fuel is collected by another optical fibre and brought to the detector.

Example 5

Figure 8:
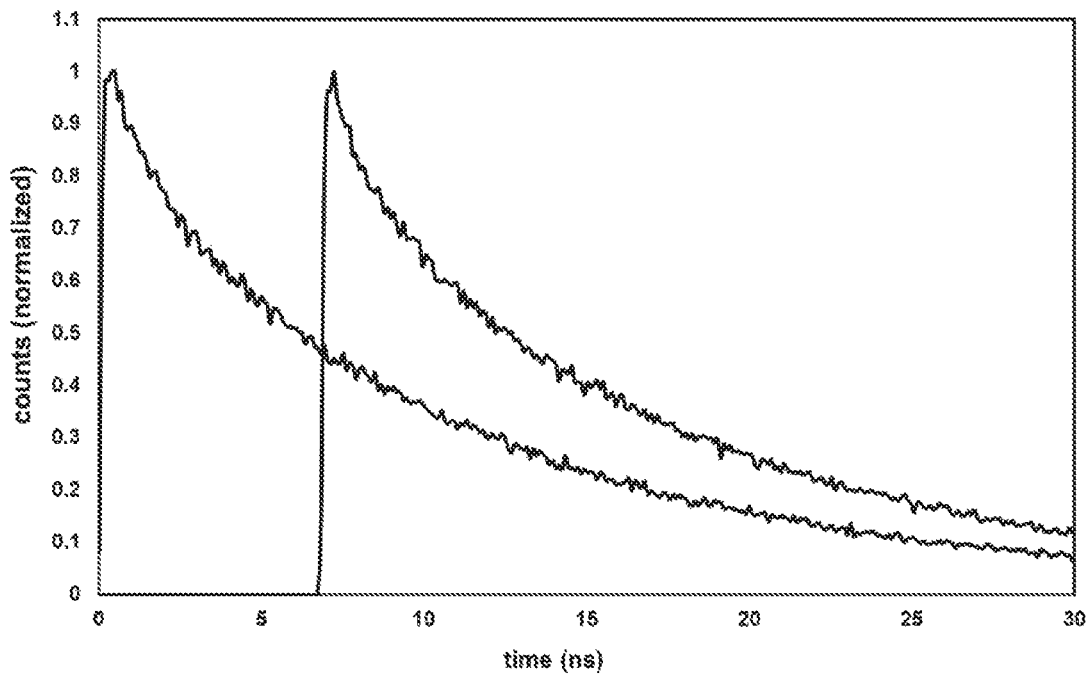
FIG. 8: Jet fuel fluorescence decay for different distances from the fuel surface to the excitation source and the detector

In another implementation of the system for measuring the fuel level in a tank, corresponding to FIG. 7, pulsed excitation light is used at a wavelength in which the radiation is practically all absorbed on the surface, namely, 300 nm. In this situation, the start of the fluorescence signal (fluorescence decay) of the fuel, measured at 345 nm, has a delay of $1/15$ ns per cm of distance from the surface of the fuel to the exit point of the radiation, at the top of the tank. FIG. 8 shows two decays with a relative delay of 7.02 ns, corresponding to a distance of 105 cm.

The invention claimed is:

1. A method for measuring a concentration of a substance or mixture of substances at various heights in a fluid, or measuring a fluid level, characterized by comprising the following steps:
   a) irradiation of the fluid with excitation light;
   b) detection of an intrinsic fluorescence light emitted by the fluid and arriving at a detector;
   c) digital processing of a signal obtained in the detector, to obtain intensity or lifetime of the intrinsic fluorescence of the fluid;
   d) conversion of the intensity or lifetime of the intrinsic fluorescence of fluid into a concentration of a substance or fluid level through a calibration.

2. A method according to claim 1 characterized by the fluid being a fuel with intrinsic fluorescence.

3. A method according to claim 2 characterized by the fluid with intrinsic fluorescence being jet aircraft fuel.

4. A method according to claim 1, characterized by the substance whose concentration at various heights is to be measured being oxygen.

5. A method for measuring a concentration of oxygen in fuel systems of jet aircraft, characterized in that it comprises the following steps:
   a) irradiating a liquid fuel or a fuel present in a free volume of a fuel tank with excitation light at a temperature range between approximately -50° C. to about 50° C.;
   b) detecting an intrinsic fluorescence light emitted by the liquid fuel or by the fuel present in the free volume and arriving at a detector;
   c) digital processing of a signal obtained in the detector, to give a value of intensity or lifetime of the intrinsic fluorescence of the fuel;
   d) conversion of the intensity or lifetime of the intrinsic fluorescence of the fuel obtained into a concentration of oxygen through a calibration.

6. A method 1 for the measurement of a level of jet fuel in a tank, characterized in that it comprises the following steps:
   a) irradiating a liquid fuel of the tank with excitation light;
   b) detecting an intrinsic fluorescence light emitted by the liquid fuel and arriving at a detector;
   c) digital processing of a signal recorded in the detector, obtaining the intrinsic fluorescence intensity response of the fuel in response to a pulsed or modulated excitation;
   d) conversion of the obtained fluorescence signal of the fuel into the liquid level, through calibration and an algorithm.

7. A method according to claim 1, characterized by the excitation light being continuous, modulated or pulsed.

8. A method according to claim 7, characterized by the excitation light being a light emitting diode or a laser.

9. A method according to claim 2, characterized by the excitation light being guided to the fuel via an optical fibre or an optical window.

10. A method according to claim 3, characterized by the fuel being one of the following: a fuel based on hydrocarbon, a fuel derived from petroleum, Jet A-1, Jet A, Jet B, TS-1, or Jet no. 3.

11. A method according to claim 10, characterized by the fuel comprising kerosene or naphtha/kerosene.

12. An optical device suitable for implementing the method of claim 1, characterized by comprising: a low intensity light source in which an excitation light is generated to irradiate a fuel; an optical fibre or optical window to guide the excitation light to the fuel; a photodetector to detect the intrinsic fluorescence of the fuel; and a signal processing unit.

13. A device according to claim 12, characterized by the excitation light source emitting continuous, modulated or pulsed light.

14. A device according to claim 13, characterized by the excitation light source being a light emitting diode or a laser.

15. A system for measuring oxygen concentration or a fuel level in a fuel tanks of jet aircraft which comprises: the optical device according to claim 13 and a fuel tank.

16. Use of the device of claim 12 for the measurement of the the concentration of a particular substance or a mixture of several substances at various heights in a fluid or measurement of the fluid level.

17. Use of the device according to claim 12 to measure the concentration of a substance or a mixture of liquid substances at various heights, or to measure the level of a liquid substance in a given container or tank.

18. Use of the device according to claim 12 for measuring the concentration of dissolved oxygen in the liquid fuel at various heights, or the fuel present in the free volume of a fuel tank of a jet aircraft.

\* \* \* \* \*